United States Patent [19]

Kipnis et al.

[11] Patent Number: 5,399,154
[45] Date of Patent: Mar. 21, 1995

[54] CONSTANT TORQUE RANGE-OF-MOTION SPLINT

[75] Inventors: Alexander Kipnis, New Hope; Yuri Belman, Plymouth, both of Minn.

[73] Assignee: Empi, Inc., St. Paul, Minn.

[21] Appl. No.: 85,758

[22] Filed: Jun. 30, 1993

[51] Int. Cl.⁶ .............................................. A61F 5/10
[52] U.S. Cl. ....................................... 602/26; 602/20; 602/16
[58] Field of Search ............... 602/26, 16, 20; 601/33, 601/34; 462/115, 118, 119, 127; 623/39

[56] References Cited

U.S. PATENT DOCUMENTS

| | | | |
|---|---|---|---|
| 42,799 | 5/1864 | Shepard . | |
| 1,847,823 | 1/1932 | Dresser . | |
| 1,851,241 | 3/1932 | Dresser . | |
| 2,413,634 | 12/1946 | Kolarik | 128/80 |
| 2,646,793 | 7/1953 | Swiech et al. | 128/80 |
| 4,180,870 | 1/1980 | Radulovic et al. | 602/20 X |
| 4,252,111 | 2/1981 | Chao et al. | 128/80 F |
| 4,397,308 | 8/1983 | Hepburn | 128/88 |
| 4,433,679 | 2/1984 | Mauldin et al. | 128/80 F |
| 4,456,002 | 6/1984 | Barber et al. | 128/77 |
| 4,485,808 | 12/1984 | Hepburn | 128/87 R |
| 4,489,718 | 12/1984 | Martin | 128/80 C |
| 4,493,316 | 1/1985 | Reed et al. | 128/80 C |
| 4,508,111 | 4/1985 | Hepburn | 128/87 R |
| 4,538,600 | 9/1985 | Hepburn | 128/88 |
| 4,602,620 | 7/1986 | Marx | 128/77 |
| 4,633,867 | 1/1987 | Kausek et al. | 128/80 C |
| 4,643,177 | 2/1987 | Sheppard et al. | 128/84 C |
| 4,657,000 | 4/1987 | Hepburn | 128/88 |
| 4,719,906 | 1/1988 | DeProspero | 128/87 A |
| 4,726,361 | 2/1988 | Farley | 128/80 B |
| 4,738,252 | 4/1988 | Friddle et al. | 128/80 H |
| 4,790,301 | 12/1988 | Silfverskiold | 128/87 A |
| 4,817,588 | 4/1989 | Bledsoe | 128/80 C |
| 4,844,057 | 7/1989 | Hoy | 128/80 C |
| 4,862,878 | 9/1989 | Davidson et al. | 602/20 |
| 4,865,024 | 9/1989 | Hensley et al. | 128/80 C |
| 5,002,045 | 3/1991 | Spademan | 602/26 X |
| 5,036,837 | 8/1991 | Mitchell et al. | 128/84 R |
| 5,052,379 | 10/1991 | Airy et al. | 602/16 |
| 5,167,612 | 12/1992 | Bonutti | 602/20 |

FOREIGN PATENT DOCUMENTS 1426580  9/1988  U.S.S.R. ...................... 602/20

Primary Examiner—Richard J. Apley
Assistant Examiner—Beverly A. Meindl
Attorney, Agent, or Firm—Kinney & Lange

[57] ABSTRACT

A range-of-motion splint for applying constant torque across a joint undergoing rehabilitative therapy. The splint includes a first brace section configured to engage a portion of a patient's body on a first side of a joint, and a second brace section configured to engage a portion of the patient's body on a second side of the joint. A first arm extends from the first brace section and a second arm extends from the second brace section. The first and second brace section arms are pivotally connected about a splint pivot axis by a pivot mechanism. A driven pulley is mounted to the second arm about the splint pivot axis. A drive pulley is rotatably mounted to the first arm about a drive axis which is spaced from the splint pivot axis. Torque is applied to the drive pulley with respect to the first arm by a spiral spring positioned about the drive axis. A belt couples the drive pulley and the driven pulley to transfer the rotation of the drive pulley to the driven pulley and apply torque between the first and second brace sections. The amount of torque applied between the brace sections can be adjusted by a torque adjusting mechanism which winds and unwinds the spring. An adjustable stop mechanism can be used to limit the range of rotational motion between the brace sections. The brace sections can be locked with respect to one another by a locking mechanism which engages and prevents movement of the drive pulley.

29 Claims, 3 Drawing Sheets

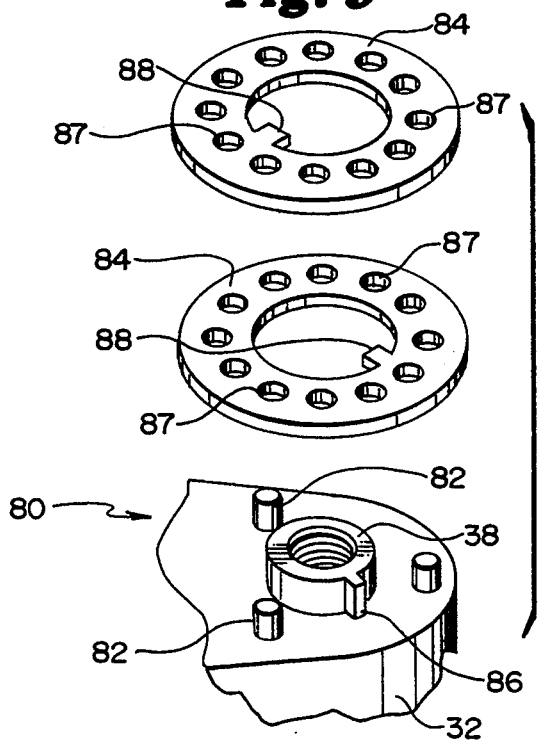
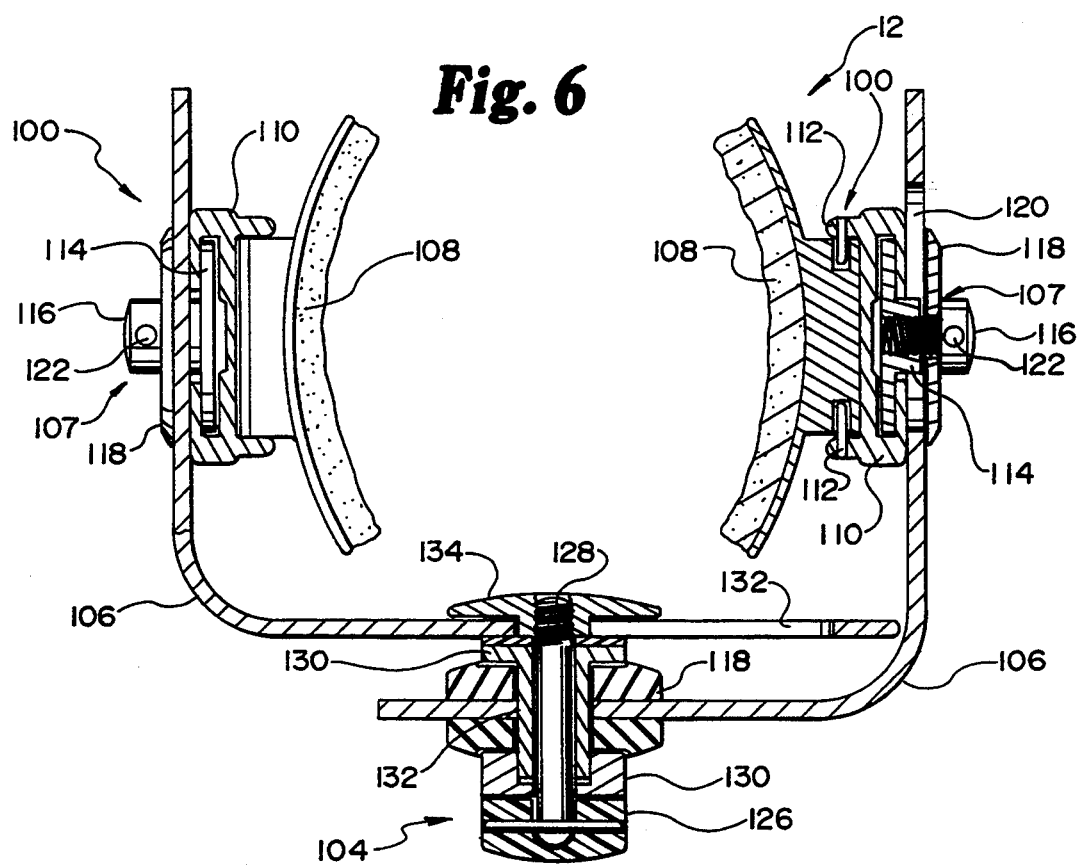

CONSTANT TORQUE RANGE-OF-MOTION SPLINT

BACKGROUND OF THE INVENTION

The present invention relates to dynamic splints or braces for applying torque across joints undergoing rehabilitative therapy.

Injuries or surgery to wrists, elbows, knees and other joints often result in flexion or extension contractures. These debilitating conditions prevent the patient from fully flexing (in the case of an extension contracture) or extending (in the case of a flexion contracture) the injured joint. Range-of-motion or ROM splints are dynamic devices commonly used during physical rehabilitative therapy to increase the range of motion over which the patient can flex or extend the joint. Splints of this type are generally known, and disclosed, for example, in the Mitchell et al. U.S. Pat. No. 5,036,837.

Commercially available range-of-motion splints typically include spring loaded brace sections for applying torque to the injured joint in opposition to the contracture. This force tends to gradually increase the working range or angle of joint motion. Springs, however, are passive devices and exert decreasing amounts of force as they retract. The amount of decrease in torque per change in the angle of the brace sections is known as the apparent elasticity of the splint. Most range-of-motion splints, therefore, require continual adjustment to maintain a constant amount of applied torque as the patient's range of joint motion increases during therapy. These torque adjusting procedures are time consuming and inconvenient.

It is evident that there is a continuing need for improved range-of-motion splints. In particular, there is a need for splints capable of applying relatively constant torque over the entire working joint angle range without adjustments. The amount of torque applied by the splint should also be adjustable to suit the needs of different patients. To be commercially viable, any such splint must be convenient to use and operate, and capable of being efficiently manufactured.

SUMMARY OF THE INVENTION

The present invention is a range-of-motion splint capable of applying relatively constant torque over the entire working range of a joint undergoing rehabilitative therapy. The splint includes first and second brace sections configured to engage portions of a patient's body on first and second sides of the joint, respectively, and a drive assembly. The first and second brace sections include first and second arms, respectively, pivotally connected about a splint pivot axis by a pivot mechanism. The drive assembly includes a driven pulley, a drive pulley, a biasing member and a linkage. The driven pulley is mounted to the second arm about the splint pivot axis. The drive pulley is mounted to the first arm about a drive axis spaced from the splint pivot axis. The biasing member is connected to the first arm and the drive pulley and applies torque to the drive pulley. The linkage couples the drive pulley to the driven pulley to apply torque between the first and second brace sections.

In one embodiment the biasing member includes a spiral spring. The spring is positioned about the drive axis and has a first end mounted to the first arm and a second end mounted to the drive pulley. The drive pulley and driven pulley are coupled by a belt.

Another embodiment of the splint includes a torque adjusting mechanism. The torque adjusting mechanism includes a worm wheel and an adjustment worm. The worm wheel is rotatably mounted to the first arm about the drive axis and is connected to the first end of the spiral spring. The adjustment worm is rotatably mounted to the first arm and engaged with the worm wheel. The adjustment worm is rotated to rotate the worm wheel and adjust the tension on the spiral spring.

In yet another embodiment the splint includes a locking mechanism for locking the angular position of the first and second brace sections with respect to one another. The locking mechanism includes a key actuated slide which engages and prevents rotation of the drive pulley.

In still another embodiment the splint includes an adjustable stop mechanism for limiting the range of motion between the first and second brace sections. The stop mechanism includes one or more washers with inwardly extending tabs rigidly mounted with respect to the first arm, and a bushing including a tab-engaging lug mounted for rotation with the driven pulley and extending into the washers. The range of rotational motion of the driven pulley is limited by engagement of the bushing lug with the washer tabs.

BRIEF DESCRIPTION OF THE DRAWINGS

FIG. 5 is an exploded perspective view of the adjustable range of motion stop mechanism of the splint shown in FIG. 1.

FIG. 6 is a sectional view of the thigh-engaging brace section of the splint shown in FIG. 1, taken along a longitudinal plane extending through the screws and bolt.

DETAILED DESCRIPTION OF THE PREFERRED EMBODIMENTS

Figure 1:
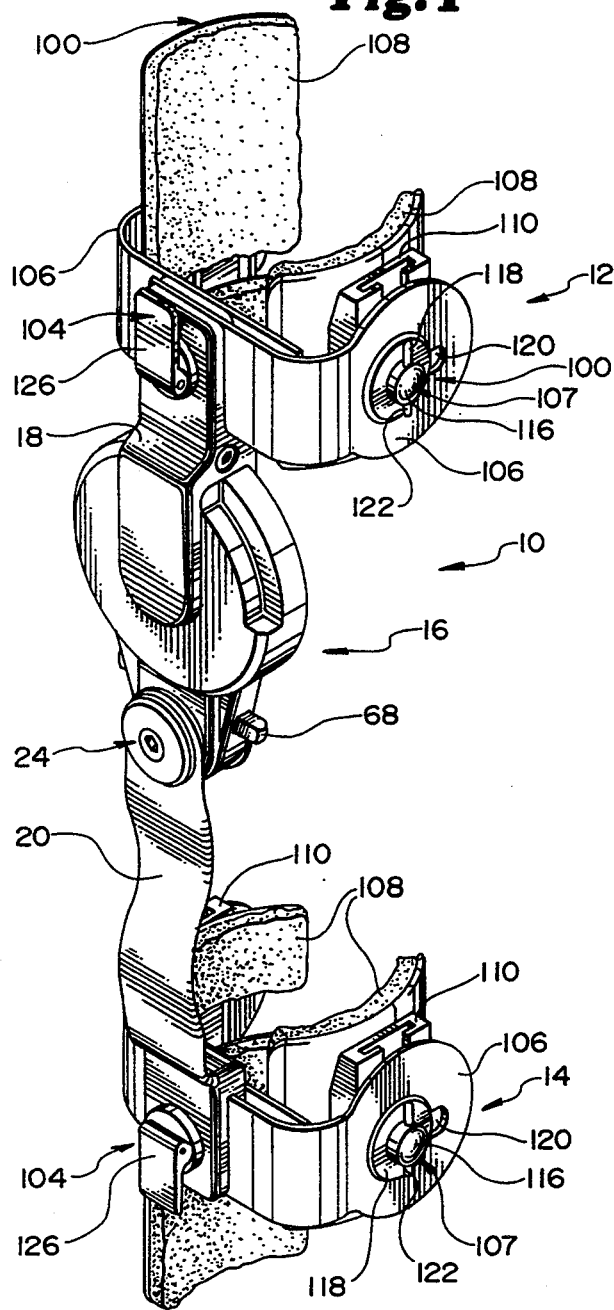
FIG. 1 is a perspective view of a range-of-motion splint in accordance with the present invention.

A constant torques dynamic range-of-motion splint 10 in accordance with the present invention is illustrated generally in FIG. 1. The illustrated embodiment of splint 10 is configured for rehabilitative knee therapy and includes a thigh-engaging brace section 12 (i.e., a first brace section for engaging a portion of the patient's body on a first side of a joint), a calf-engaging brace section 14 (i.e. a second brace section for engaging a portion of the patient's body on a second side of a joint), and constant torque drive assembly 16. Brace sections 12 and 14 include first and second arms 18 and 20, respectively, which are connected about a first or splint pivot axis by pivot mechanism 24. During used the positions of brace sections 12 and 14 on the patient's leg are adjusted to align the splint pivot axis with the rotational axis of the knee. Drive assembly 16 provides relatively constant torque in opposition to contractures over the entire range of knee motions thereby alleviating the need for torque adjustments as the injury heals and the range of motion increases.

Drive assembly 16 can be described with reference to FIGS. 2–4. As shown, drive assembly 16 includes a drive mechanism 26 and a driven mechanism 28 mechanically interconnected by a linkage such as belt 30. Arm 18 includes baseplate 32. Driven mechanism 26, driven mechanism 28 and belt 30 are positioned within a housing formed by baseplates 32 and 34. Driven mechanism 28 includes flange 36, bushing 38 and driven pulley 42, all of which are fastened together by threaded shaft 40 which defines the splint pivot axis. Flange 36 is fastened to arm 20 of calf-engaging brace section 14 by rivets 44, and journaled into an aperture through baseplate 34 for rotation about the splint pivot axis. A cap 48 including threaded shaft 40 is secured to the side of flange 36 opposite baseplate 34. Bushing 38 is journaled into an aperture through baseplate 32 by bushing 46, also for rotation about the splint pivot axis. Torque applied to driven pulley 42 by drive mechanism 26 therefore rotates calf-engaging brace section 14 with respect to thigh-engaging brace section 12.

Drive mechanism 26 is mounted to arm 18 of thigh-engaging brace section 12 at a location spaced from driven mechanism 28 and the splint pivot axis, and includes a biasing member such as spring 50 for generating a bias torque. The bias torque generated by spring 50 is coupled to driven mechanism 28 by belt 30. In the embodiment shown, drive mechanism 26 includes worm wheel 52, adjustment worm 54 and drive pulley 56. Drive pulley 56 is mounted for rotation about a drive axis by a bearing 58 which includes a shaft 67 mounted for rotation about bearing sections 61 and 63. Bearing sections 61 and 63 secured to baseplates 32 and 34 by screws 60 and 65, respectively. Drive pulley 56 is press-fit onto shaft 67.

Worm wheel 52 is a ring-shaped member concentrically positioned with respect to drive pulley 56 in a recess in baseplate 32. Spring 50 is a spiral-type spring in the embodiment shown, and is wound around drive pulley 56 within worm wheel 52. A first end 62 of spring 50 is engaged with worm wheel 52. The second end 64 of spring 50 is engaged with drive pulley 56 by means of shaft 67. Adjustment worm 54 is positioned within recesses in baseplates 32 and 34 for engagement with the worm wheel 52 and rotation about an axis perpendicular to the drive axis. Adjustment worm 54 and worm wheel 52 function as a torque adjusting mechanism. As shown in FIG. 1 and 4, ends of adjustment worm 54 extend into recesses in the outside of baseplates 32 and 34. A key or other wrench (not shown) can be used to rotate adjustment worm 54, thereby rotating worm wheel 52 to wind and unwind spring 50 in order to increase or decrease the amount of torque applied to drive pulley 56 by the spring.

Figure 2:
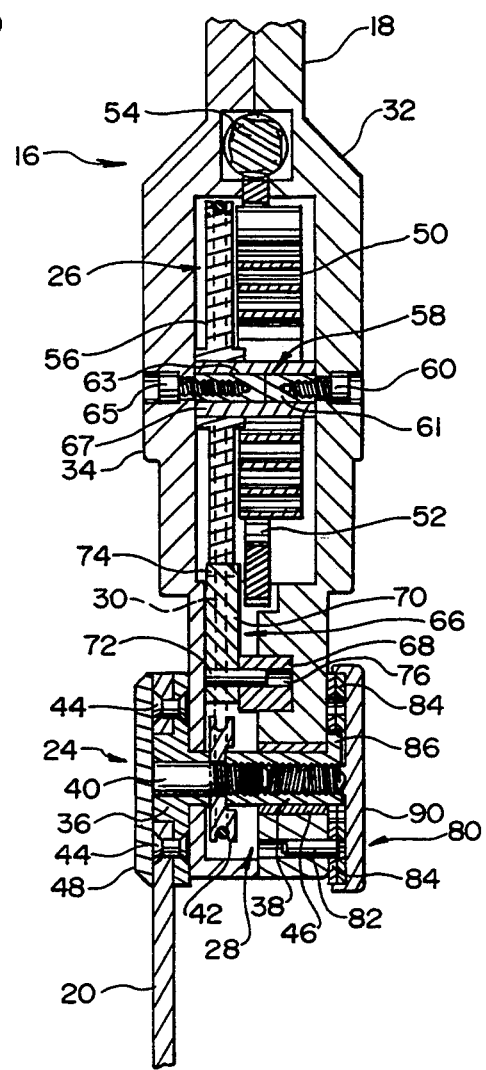
FIG. 2 is a sectional view of the drive assembly shown in FIG. 1, taken along a longitudinal plane extending through the center of the drive and driven mechanisms.
Figure 3:
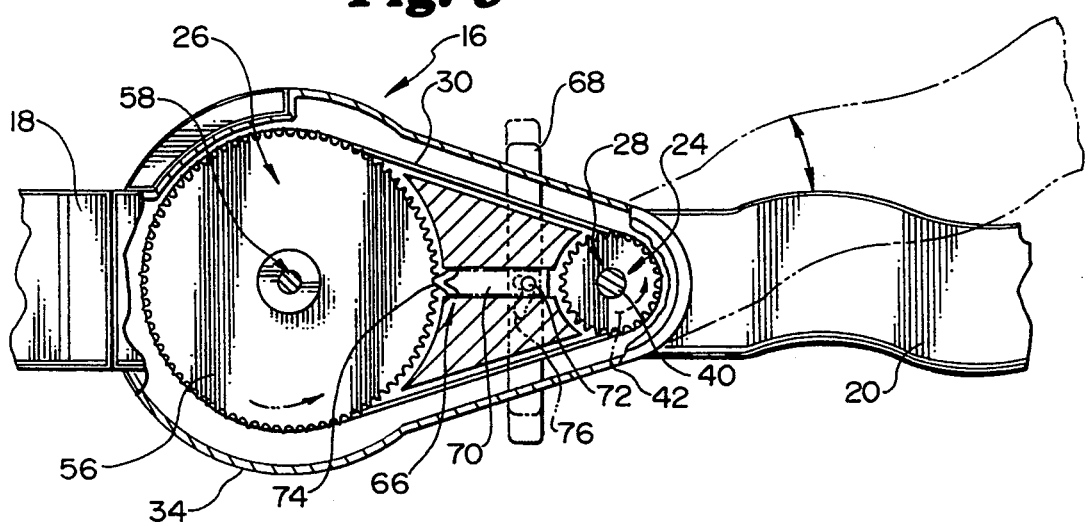
FIG. 3 is a side view of the drive assembly shown in FIG. 1, with portions thereof cut away to illustrate the drive pulley, driven pulley and locking mechanism.
Figure 4:
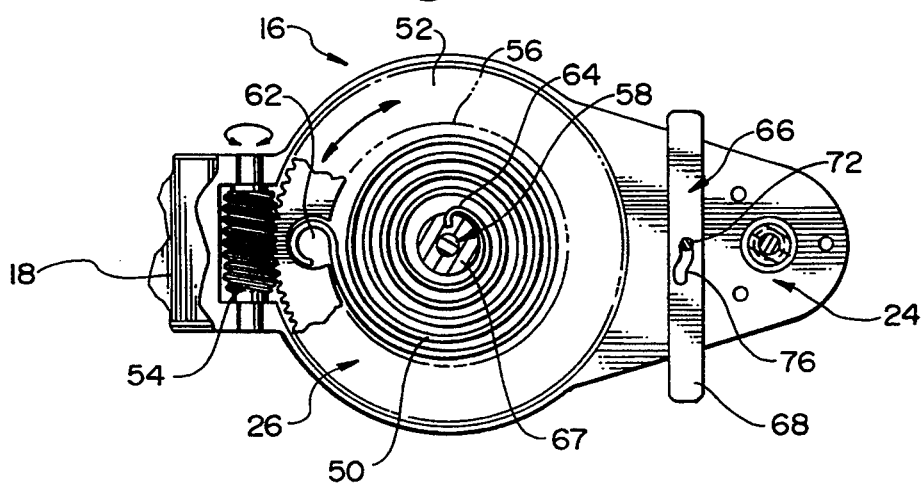
FIG. 4 is a side view of the drive assembly shown in FIG. 1, with portions thereof cut away to illustrate the coil spring and torque adjusting mechanism.

Although shown as round pulleys of constant radii in FIGS. 2 and 3, driven pulley 42 and drive pulley 56 can be eccentric (i.e., have varying radii) to compensate for slight variations in the torque generated by spring 50 as it is wound and unwound, or to otherwise vary the relationship between the splint angle and applied torque. Alternatively, gears (not shown) can be substituted for pulleys 42 and 56, with the teeth of the gears functioning as the linkage.

A locking mechanism 66 prevents relative movement between brace sections 12 and 14. In the embodiment shown, locking mechanism 66 includes key 68, slide 70 and pin 72. Slide 70 is positioned in a recess in baseplate 34 that guides the slide for motion along a linear path toward and away from drive pulley 56. Slide 70 includes a teeth-engaging tip 74 on the end adjacent drive pulley 56. Pin 72 is mounted to and extends from slide 70. Key 68 is positioned in a recess in baseplate 34 that guides the key for motion along a linear path generally perpendicular to that of slide 70, and includes an elongated slot 76 which extends at a non-parallel angle with respect to the key path of motion. Opposite ends of key 68 extend beyond the baseplate 34. Pin 72 extends into slot 76 and couples the motion of key 68 to slide 70. By engaging the ends of key 68, the patient or clinician can force the key back and forth along its path of motion, and engage and disengage slide tip 74 with the teeth of drive pulley 56. Brace sections 12 and 14 can therefore be conveniently and rigidly locked with respect to one another at any position within the range of motion over which splint 10 is configured for operation.

An adjustable range-of-motion stop mechanism 80 enables a clinician to control the range of rotational motion between brace sections 12 and 14. As perhaps best shown in FIGS. 2 and 5, stop mechanism 80 includes pins 82, stop washers 84 and a lug 86 which extends from bushing 38 of driven mechanism 28. Three pins 82 are circumferentially positioned around the splint pivot axis and extend from baseplate 32. Washers 84 each include a plurality of circumferentially spaced apertures 87 and a tab 88 that extends into the central aperture of the washer. Washer apertures 87 are spaced so they can be received by pins 82 with tabs 88 at any desired circumferential position. Washers 84 are placed on top of one another on pins 82 with tabs 88 positioned to engage bushing lug 86 at the desired stop points. Cap 90 covers washers 84 and is screwed into bushing 38 to secure the washers in place. Since bushing 38 rotates with driven mechanism 28, the range of rotational motion between brace sections 12 and 14 is limited by the engagement of lug 86 with washer tabs 88. A clinician can conveniently remove cap 90 and reposition washers 84 to increase and decrease the range of motion over which splint 10 can operate as the patient's condition improves.

Brace sections 12 and 14 can be described in greater detail with reference to FIGS. 1 and 6. As shown, thigh-engaging brace section 12 includes front and back thigh sections 100 which are adjustably mounted to arm 18 by over-center clamp 104. Each thigh section 100 includes a right angle bracket 106 having one end mounted to arm 18. Front and back thigh supports 108 are adjustably mounted to the other end of brackets 106 by clamps 107. Brackets 106 position the front and back thigh supports 108 adjacent the front and back, respectively, of the patient's thigh, while leaving the side of the splint opposite drive assembly 16 open. Splint 10 can therefore be conveniently positioned on the patient's leg from the side.

Clamps 107 for mounting thigh supports 108 to brackets 106 include elongated, slotted tracks 110, track followers 114, screws 116 and washers 118. Thigh supports 108 are pivotally mounted to tracks 110 by pins 112. Track followers 114 are slidably mounted within tracks 110. Thigh supports 108 are secured to brackets 106 by screws 116 which extend through washers 118, elongated apertures 120 in the brackets, and into threaded apertures in track followers 114. Slotted tracks 110 are configured for orientation about an axis parallel to the patient's leg, while the slotted apertures 120 in brackets 106 are configured for orientation perpendicular to the leg. The position of thigh supports 108 can therefore be adjusted to fit the patient, and securely clamped to brackets 106 using handles 122 on screws 116.

Clamp 104 includes an over-center handle 126 pivotally connected to threaded bolt 128. Bolt 128 extends through brace arm 18, clamp bushings 130 and elongated apertures 132 in brackets 106. Elongated apertures 132 are configured for orientation perpendicular to the patient's leg so the thigh sections 100 can be opened and closed to facilitate the application and removal of splint 10. When thigh supports 100 are properly positioned, brackets 106 are clamped to brace arm 18 through actuation of over-center handle 126.

Other than the size of the components, which are configured for the patient's calf rather than thigh, calf-engaging brace section 14 is structurally and operationally identical to thigh-engaging brace section 12 described above. Brace sections 12 and 14 can be conveniently applied, adjusted and removed by the patient or clinician to comfortably yet securely fit patients having differently sized legs. Supports 100 of different sizes can also be conveniently mounted to arms 18 and 20 to enable splint 10 to be used for both flexion and extension contractures on limbs on both sides of a patient.

Range-of-motion splint 10 offers considerable advantages over those shown in the prior art. The adjustable brace sections enable the splint to be quickly and conveniently positioned on and removed from the patient. These brace sections can also be adjusted over a relatively large range enabling the splint to be comfortably and securely fit to patients of different sizes.

When the drive and driven pulleys have different diameters with a ratio designated N, the apparent elasticity of the splint is reduced by a factor $N^2$ from that of the spring. Specifically; if the drive pulley is rotated $\Delta \alpha$ degrees, and the torque at the drive pulley has changed by $\Delta T$, the driven pulley will have rotated $N\Delta \alpha$ degrees and the torque at the driven pulley will have changed by $\Delta T/N$. The elasticity at the drive pulley is therefore $\Delta T/\Delta \alpha$, while the elasticity at the driven pulley is $(\Delta T/N)/N\Delta \alpha$, $N^2$ times lower than that at the drive pulley. Relatively constant torque can therefore be applied over the working joint angle range without the need for adjustments.

The amount of torque applied by the splint can be easily adjusted with the torque adjustment mechanism to accommodate the needs of different patients. The range of joint motion over which the splint operates can also be conveniently adjusted with the stop mechanism. The use of the lock mechanism enables the patient to conveniently and comfortably position and remove the brace.

Although the present invention has been described with reference to preferred embodiments, those skilled in the art will recognize that changes can be made in form and detail without departing from the spirit and scope of the invention.

What is claimed is:

1. A range-of-motion splint for applying torque to a joint undergoing rehabilitative therapy, including:
    a first brace section configured to engage a portion of a body on a first side of a joint, the first brace section including a first arm;
    a second brace section configured to engage a portion of a body on a second side of a joint, the second brace section including a second arm;
    a pivot mechanism for pivotally connecting the first and second arms about a splint pivot axis;
    a driven pulley mounted to the second arm about the splint pivot axis;
    a drive pulley rotatably mounted to the first arm about a drive axis, the drive axis spaced from the splint pivot axis;
    a biasing member connected to the first arm and the drive pulley, for applying torque to the drive pulley with respect to the first arm; and
    a linkage coupling the drive pulley to the driven pulley, for transferring the torque from the drive pulley to the driven pulley to apply torque between the first and second brace sections.

2. The range-of-motion splint of claim 1 wherein the biasing member includes a spiral spring.

3. The range-of-motion splint of claim 1 wherein the linkage includes engaged teeth on the drive pulley and the driven pulley.

4. The range-of-motion splint of claim 1 wherein the linkage includes a belt coupling the drive pulley to the driven pulley.

5. The range-of-motion splint of claim 1 wherein at least one of the drive and driven pulleys includes an eccentric pulley.

6. The range-of-motion splint of claim 1 and further including a torque adjusting mechanism for adjusting the torque applied between the first and second brace sections.

7. The range-of-motion splint of claim 6 wherein:
    the biasing member includes a spiral spring positioned about the drive axis and having first and second ends, the first end connected to the first arm and the second end connected to the drive pulley; and
    the torque adjusting mechanism includes a mechanism for adjusting tension on the spiral spring.

8. The range-of-motion splint of claim 7 wherein the torque adjusting mechanism includes:
    a worm wheel rotatably mounted to the first arm, the first end of the spiral spring connected to the worm wheel; and
    an adjustment worm rotatably mounted to the first arm and engaged with the worm wheel, for rotating the worm wheel to adjust the tension on the spiral spring.

9. The range-of-motion splint of claim 1 and further including a locking mechanism for locking the angular position of the first and second brace sections with respect to one another.

10. The range-of-motion splint of claim 9 wherein the locking mechanism includes a mechanism for engaging and preventing rotation of the drive pulley.

11. The range-of-motion splint of claim 1 and further including an adjustable stop mechanism for limiting the range of motion between the first and second brace sections.

12. The range-of-motion splint of claim 11 wherein the stop mechanism includes a mechanism for limiting the range of rotational motion of the driven pulley.

13. The range-of-motion splint of claim 12 wherein the stop mechanism includes:
    one or more washers with inwardly extending tabs rigidly mounted with respect to the first arm, and
    a bushing including a tab-engaging lug mounted for rotation with the driven pulley and extending into the washers, the range of rotational motion of the driven pulley limited by engagement of the bushing lug with the washer tabs.

14. The range-of-motion splint of claim 13 and including a releasable mechanism for mounting the washers with respect to the first arms so the positions of the tabs and the range of rotational motion of the driven pulley can be adjusted.

15. The range-of-motion splint of claim 14 wherein the releasable mechanism for mounting the washers with respect to the first arm includes:
   pins extending from the first arm; and
   apertures in the washers for mounting the washers on the pins.

16. The range-of-motion splint of claim 1 and further including a housing for the driven pulley, drive pulley and linkage.

17. A range-of-motion splint for applying torque to a joint undergoing rehabilitative therapy, including:
   a first brace section configured to engage a portion of a body on a first side of a joint, the first brace section including a first arm;
   a second brace section configured to engage a portion of a body on a second side of a joint, the second brace section including a second arm;
   a pivot mechanism for pivotally connecting the first and second arms about a splint pivot axis;
   a driven pulley mounted to the second arm about the splint pivot axis;
   a drive pulley rotatably mounted to the first arm about a drive axis, the drive axis spaced from the splint pivot axis;
   a spiral spring positioned about the drive axis and connected to the first arm and the drive pulley, for applying a rotational bias force to the drive pulley with respect to the first arm; and
   a linkage coupling the drive pulley to the driven pulley to transfer the rotational bias force from the drive pulley to the driven pulley and apply torque between the first and second brace sections.

18. The range-of-motion splint of claim 17 and further including a torque adjusting mechanism for adjusting the tension of the spiral spring.

19. The range-of-motion splint of claim 18 wherein the torque adjusting mechanism includes:
   a worm wheel rotatably mounted to the first arms the first end of the spiral spring connected to the worm wheel; and
   an adjustment worm rotatably mounted to the first arm and engaged with the worm wheel, for rotating the worm wheel to adjust the tension on the spiral spring.

20. The range-of-motion splint of claim 17 and further including an adjustable stop mechanism for limiting the range of motion between the first and second brace sections.

21. The range-of-motion splint of claim 20 wherein the stop mechanism includes a mechanism for limiting the range of rotational motion of the driven pulley.

22. The range-of-motion splint of claim 21 wherein the stop mechanism includes:
   one or more washers with inwardly extending tabs rigidly mounted with respect to the first arm, and
   a bushing including a tab-engaging lug mounted for rotation with the driven pulley and extending into the washers, the range of rotational motion of the driven pulley limited by engagement of the bushing lug with the washer tabs.

23. The range-of-motion splint of claim 22 and including a releasable mechanism for mounting the washers with respect to the first arm, so the positions of the tabs and the range of rotational motion of the driven pulley can be adjusted.

24. The range-of-motion splint of claim 23 wherein the releasable mechanism for mounting the washers with respect to the first arm includes:
   pins extending from the first arm; and
   apertures in the washers for mounting the washers on the pins.

25. The range-of-motion splint of claim 20 and further including a locking mechanism for locking the angular position of the first and second brace sections with respect to one another.

26. The range-of-motion splint of claim 25 wherein the locking mechanism includes a mechanism for engaging and preventing rotation of the drive pulley, 27. The range-of-motion splint of claim 17 wherein at least one of the drive pulley and driven pulley includes an eccentric pulley.

28. In a range-of-motion splint of the type including first and second brace sections for engaging portions of a patient's body on opposite sides of a joint undergoing rehabilitative therapy, a pivot mechanism for pivotally connecting the first and second brace sections for movement over a range of motion, and a drive assembly including a drive pulley for applying torque between the first and second brace sections, the improvement characterized by a locking mechanism including a mechanism for engaging and preventing rotation of the drive pulley, for releasably locking the position of the first and second brace sections with respect to one another at each of a plurality of positions along the range of motion.

29. The range-of-motion splint of claim 28 wherein:
   the drive pulley includes teeth; and
   the locking mechanism includes a mechanism for engaging the teeth of the drive pulley.

* * * * *

UNITED STATES PATENT AND TRADEMARK OFFICE
CERTIFICATE OF CORRECTION

PATENT NO. : 5,399,154

DATED : March 21, 1995

INVENTOR(S) : ALEXANDER KIPNIS, YURI BELMAN

It is certified that error appears in the above-indentified patent and that said Letters Patent is hereby corrected as shown below:

Col. 2, line 64, delete "used", insert --use--

Col. 7, line 45, delete "arms", insert --arm,--

Signed and Sealed this

Twentieth Day of June, 1995

Attest:

BRUCE LEHMAN

Attesting Officer     Commissioner of Patents and Trademarks